(12) United States Patent
Muraca (10) Patent No.: US 6,582,967 B2
(45) Date of Patent: Jun. 24, 2003

(54) METHOD OF FORMING A MICROARRAY FROM FROZEN TISSUE

(75) Inventor: Patrick J. Muraca, Pittsfield, MA (US)

(73) Assignee: Clinomics Biosciences, Inc., Pittsfield, MA (US)

( * ) Notice: Subject to any disclaimer, the term of this patent is extended or adjusted under 35 U.S.C. 154(b) by 29 days.

(21) Appl. No.: 09/910,172

(22) Filed: Jul. 20, 2001

(65) Prior Publication Data

US 2002/0106626 A1 Aug. 8, 2002

Related U.S. Application Data

(62) Division of application No. 09/779,753, filed on Feb. 8, 2001.

(51) Int. Cl.$^7$ .................................................. G01N 1/08
(52) U.S. Cl. ........................ 436/174; 436/63; 435/40.5; 435/40.52
(58) Field of Search ............................ 435/40.5, 40.52, 435/1.3, 6, 287.3, 286.3, 286.2, 309.1, 307.1; 422/63, 65, 68.1, 99; 436/63, 174; 600/566, 567; 73/864.44, 864.45

(56) References Cited

U.S. PATENT DOCUMENTS

| | | | |
|---|---|---|---|
| 4,914,022 A | * | 4/1990 | Furmanski et al. ...... 435/40.52 |
| 5,804,384 A | | 9/1998 | Muller et al. .................. 435/6 |
| 5,994,133 A | * | 11/1999 | Meijs et al. ................ 435/395 |
| 6,103,479 A | | 8/2000 | Taylor ........................ 435/7.2 |
| 6,103,518 A | | 8/2000 | Leighton .................. 435/286.3 |
| 6,165,709 A | | 12/2000 | Friend et al. .................. 435/4 |
| 6,406,840 B1 | * | 6/2002 | Li et al. ...................... 435/1.3 |

FOREIGN PATENT DOCUMENTS

| | | |
|---|---|---|
| EP | 0 238 190 | 9/1997 |
| EP | 1 026 260 | 8/2000 |
| WO | 99/43855 | 9/1999 |
| WO | 99/44062 | 9/1999 |
| WO | 99/44063 | 9/1999 |
| WO | 00/24940 | 5/2000 |

OTHER PUBLICATIONS

Moch, et al., "Tissue Microarrays: What Will They Bring to Molecular and Anatomic Pathology," Advances in Anatomic Pathology 8(1): Jan. 14–20, 2001.

* cited by examiner

Primary Examiner—William H. Beisner
(74) Attorney, Agent, or Firm—Palmer & Dodge, LLP (57) ABSTRACT

A device particularly suited for constructing frozen tissue microarrays. The device comprises: a cooling chamber for receiving at least one frozen material and for maintaining the frozen material in a frozen condition; the cooling chamber moveable in an x and y direction relative to a horizontal surface; at least one coring needle comprising a cutting surface and a lumen for receiving a core of frozen material cut by the cutting surface; and at least one coring needle positioning element, for positioning the at least one coring needle over said frozen material for cutting said frozen material. Frozen tissue microarray blocks and methods of generating these are also provided.

24 Claims, 6 Drawing Sheets

METHOD OF FORMING A MICROARRAY FROM FROZEN TISSUE

RELATED APPLICATIONS

This application claims priority under 35 U.S.C. §120 as a Divisional of U.S. application Ser. No. 09/779,753 filed Feb. 8, 2001, the entirety of which is incorporated herein by reference.

FIELD OF INVENTION

The invention relates to a tissue microarrayer for arraying frozen tissue samples and a method of using the same. The device may be operated automatically, semi-automatically, or manually.

BACKGROUND OF THE INVENTION

Tissue microarrays increase the throughput of molecular analyses by simultaneously arraying proteins, nucleic acids, and other biomolecules. Methods of generating tissue microarrays generally include removing tissue slices or cores from paraffin blocks and re-embedding these. For example, Battifora, Laboratory Investigation, 55:244–248, 1986; and U.S. Pat. No. 4,820,504, teaches forming multiple tissue samples into rods, bundling the rods into a casing, embedding the encased rods in paraffin and sectioning them. Although the method arrays multiple tissue samples, it is difficult to determine the identity of tissues within the array.

In U.S. Pat. No. 5,002,377, Battifora describes cutting tissue samples into strips, positioning the strips into parallel grooves in a mold, and embedding the strips in paraffin. Embedded strips are stacked, forming an embedded block comprising multiple tissue samples. The method is time consuming and is performed manually.

An automatic tissue microarrayer is described in U.S. Pat. No. 6,103,518, the entirety of which is incorporated herein by reference. The arrayer comprises two hollow needle punches; one for punching a hole in a recipient block comprising paraffin and one for removing a core of paraffin-embedded tissue from a sample or donor block. A stylet is used to remove the core of tissue from the donor punch and to push the core of tissue into the hole left in the recipient block. A different stylet is used to remove embedding matrix from the recipient punch so that it can be reused. The stylet is in communication with a stylet driver which controls its movement. The device and stylets described in U.S. Pat. No. 6,103,518 can be used to array multiple tissue samples; however, the device is not designed to optimally array a plurality of frozen tissue samples. Similarly, the stylet used with the device is subject to breakage upon repeated use in arraying frozen tissues.

SUMMARY OF THE INVENTION

The invention provides a device for microarraying tissue samples which is particularly suited for arraying frozen tissue samples. In one embodiment, the device comprises a cooling chamber for receiving at least one frozen material and for maintaining the frozen material in a frozen condition. The cooling chamber is moveable in an x- and y-direction relative to a horizontal surface. The device further comprises at least one coring needle which comprises a cutting surface and a lumen for receiving a core of frozen material cut by the cutting surface. In one embodiment, the device comprises at least one coring needle positioning element for positioning the at least one coring needle over said frozen material for cutting said frozen material. The coring needle can core either, or both, of a frozen tissue sample or frozen embedding matrix.

In another embodiment of the invention, the coring needle is in communication with a stylet, the stylet for ejecting the frozen material from the lumen of the coring needle. In one embodiment, the stylet comprises a stylet needle having a pushing surface and the stylet needle slidably fits within the lumen of the coring needle.

In another embodiment, device further comprises a processor in communication with the positioning element, and the processor controls the movement of the coring needle. In a further embodiment, the device further comprises a processor in communication with the stylet and controls the movement of the stylet.

In one embodiment, the positioning element is moveable in an x-direction relative to a fixed horizontal surface positioned beneath the cooling chamber. In another embodiment, the positioning element is moveable in a y-direction relative to a fixed horizontal surface positioned beneath said cooling chamber. In a further embodiment, the device further comprises at least one platform, moveable in an x- or y-direction relative to a fixed horizontal surface positioned beneath the cooling chamber, and the at least one platform is between the cooling chamber and the fixed horizontal surface. In still another embodiment, the at least one platform comprises a first and a second platform. The first platform is moveable in an x-direction, while the second platform is moveable in a y-direction relative to the fixed horizontal surface.

In one embodiment, the device comprises a first and second coring needle, the first coring needle for receiving a frozen tissue sample from a block of frozen tissue, the second coring needle for receiving frozen embedding matrix from a block of frozen embedding matrix.

In one embodiment, the at least one positioning element comprises a recess for receiving the at least one coring needle and the at least one coring needle is capable of rotating within the recess of said at least one positioning element. In another embodiment, the device comprises a first positioning element for receiving a first coring needle and a second positioning element for receiving a second coring needle. In a further embodiment, the first and second positioning element are coupled to a holder. In still a further embodiment, the first and second positioning elements move in identical increments.

In one embodiment, the at least one positioning element is coupled to an x-direction slide element for moving the at least one positioning element in an x-direction relative to a fixed horizontal surface. In another embodiment, the at least one positioning element is coupled to a z-direction slide element. In a further embodiment, the z-direction slide element is coupled to a z-direction slide plate and is slidable along the z-direction slide plate in a z-direction. In still a further embodiment, the z-direction slide plate is coupled to the horizontal surface. In one embodiment, the x-direction slide is coupled to an x-direction slide plate and is slideable along the x-direction slide plate in an x-direction.

In one embodiment of the invention, when the first positioning element is positioned over a frozen tissue sample, the second positioning element is positioned over a block of frozen embedding matrix. In another embodiment, the device further comprises a moveable bridge for supporting a block of first frozen material over a block of second frozen material (e.g., a block of donor tissue over a block of frozen embedding matrix).

In one embodiment, the device comprises at least one motor for driving the movement of at least one moveable element of the device. In another embodiment, the at least one motor is in communication with a processor which is connectable to the network.

In one embodiment, the cooling chamber is sized to receive a donor block comprising a frozen tissue sample and a recipient block comprising frozen embedding matrix. In one embodiment, the donor and recipient block are contained within a retaining chamber within the cooling chamber.

In one embodiment, the device comprises a platform beneath the cooling chamber and a processor in communication with the platform controls the movement of the platform. In one embodiment, the device further comprises an input unit in communication with the processor. In this embodiment, when a user inputs coordinates into said input unit, the processor moves the at least one platform to the inputted coordinates.

The invention further provides a method of arraying frozen tissues comprising: providing a donor block comprising a frozen tissue sample, providing a recipient block comprising a frozen embedding matrix (the recipient block having at least one hole for receiving a core of frozen tissue), obtaining a core of frozen tissue from the donor block, and placing the core of tissue in the hole in the recipient block. In one embodiment, the method further comprises the step of placing the donor and recipient blocks in a cooling chamber. In one embodiment, the step of obtaining the core of frozen tissue comprises coring the frozen tissue with a coring needle. In another embodiment, the method further comprises: obtaining a section of tissue from the donor block, identifying coordinates of a tissue sample of interest in the section; and obtaining the core of frozen tissue from a portion of the donor block comprising identical coordinates. In one embodiment, the identifying is performed using a microscope. In another embodiment, the tissue sample of interest comprises abnormally proliferating cells. In a further embodiment, the tissue sample of interest comprises at least one cell expressing a heterogeneously expressed biomolecule.

In one embodiment, the method of arraying frozen tissues comprises providing a donor block comprising a frozen tissue sample, providing a recipient block comprising a frozen embedding matrix, creating at least one hole in the recipient block for receiving a core of frozen tissue, obtaining a core of frozen tissue from the donor block, and placing the core of tissue in the hole in said recipient block. In one embodiment, the steps of obtaining the core from the donor block and creating the hole in the recipient block are performed simultaneously. In another embodiment, the steps of obtaining the core from the donor block and creating the hole in the recipient block are performed sequentially. In a further embodiment, the method is at least partially automated.

The invention further provides microarray blocks for generating a plurality of microarrays. In one embodiment, the microarray block comprises a block of frozen embedding matrix comprising a plurality of holes, each hole filled with a frozen tissue sample. In one embodiment, the plurality of holes comprise tissue samples from at least two different organs of a single individual. In a further embodiment, the plurality of holes comprise tissue samples from at least five different organs of a single individual.

In one embodiment, the microarray block comprises at least one hole filled with a core of tissue comprising abnormally proliferating cells. In another embodiment, the microarray block comprises at least one tissue core at least 0.6 mm in diameter, at least 2 mm in diameter, or larger than 2 mm in diameter. In one embodiment, at least one tissue core comprises non-cancerous tissues.

In one embodiment, the microarray block comprises at least one tissue core from a human, from a plant, and/or from a non-human mammal. In one embodiment, at least one tissue core is from an organism selected from the group consisting of: dictostyelium, hydra, a nematode, a fruit fly, zebrafish, a frog, a mouse, a rat, a rabbit, a cat, a dog, a primate, and a plant. In another embodiment, the plurality of tissue cores comprise a plurality of different tissues' at different developmental stages. In a further embodiment, the microarray block comprises cores of tissue from population of individuals. In still a further embodiment, the microarray block comprises cores of tissues representing different stages of a disease, such as cancer.

In one embodiment, the microarray block is further associated with an identifier, and information relating to the identifier stored within a database. In one embodiment, the information comprises information relating to the source of each tissue core within the microarray.

In one embodiment, the microarray block comprises tissue from at least one organism comprising an exogenous nucleic acid sequence which has been introduced into said organism. In another embodiment, the organism is a transgenic animal or plant. In one embodiment, the organism is a knock-out mouse or a knock-in mouse. In another embodiment, the microarray comprises a plurality of tissue samples, each tissue sample expressing different doses of a gene.

BRIEF DESCRIPTION OF THE DRAWING

The objects and features of the invention can be better understood with reference to the following detailed description and accompanying drawings. Like features are represented with the same numbers throughout the drawings. The drawings are not to scale.

DETAILED DESCRIPTION OF THE INVENTION

The invention provides a device which is particularly suited for generating frozen tissue microarrays. The device is capable of assembling hundreds of frozen tissue samples into a block of embedding matrix for subsequent sectioning and placement onto a substrate.

Definitions

In order to more clearly and concisely describe and point out the subject matter of the claimed invention, the following definitions are provided for specific terms which are used in the following written description and the appended claims.

As defined herein, a "tissue" is an aggregate of cells that perform a particular function in an organism. The term "tissue" as used herein refers to cellular material from a particular physiological region. The cells in a particular tissue may comprise several different cell types. A non-limiting example of this would be brain tissue that further comprises neurons and glial cells, as well as capillary endothelial cells and blood cells. The term "tissue" also is intended to encompass a plurality of cells contained in a sublocation on the tissue microarray that may normally exist as independent or non-adherent cells in the organism, for example immune cells, or blood cells. The term is further intended to encompass cell lines and other sources of cellular material that now exist which represent specific tissue types (e.g., by virtue of expression of biomolecules characteristic of specific tissue types).

As defined herein a "a tissue sample" refers to a fragment, slice, or suspension of tissue cells (e.g., from a cell line).

As defined herein, "a tissue microarray" is a microarray that comprises a plurality of sublocations, each sublocation comprising tissue cells and/or extracellular materials from tissues, or cells typically infiltrating tissues, where the morphological features of the cells or extracellular materials at each sublocation are visible through microscopic examination. The term "microarray" implies no upper limit on the size of the tissue sample on the array, but merely encompasses a plurality of tissue samples which, in one embodiment, can be viewed using a microscope.

The term "donor block" as used herein, refers to tissue embedded in an embedding matrix, from which a tissue sample can be obtained and placed directly onto a slide or placed into a receptacle of a recipient block. The term "block" as used herein does not imply any limiting shape, and blocks according to the invention can be cube shaped, disc-shaped, and other shapes.

The term "recipient block" as used herein, refers to a block formed from an embedding matrix, which comprises a plurality of tissue samples; each tissue sample forming the source of a sublocation on a tissue microarray. The relative positions of tissue samples are maintained when the recipient block is sectioned, such that each section comprises sublocations at identical coordinates as any other section from the recipient block.

As used herein, a "microarray block" refers to a block of embedding matrix comprising a plurality of tissue cores, and each section of the block can be used to generate a microarray. A microarray block is a recipient block into which all desired tissue cores have been placed.

As defined herein, a "molecular probe" is any detectable molecule, or is a molecule which produces a detectable molecule upon reacting with a biological molecule. "Reacting" encompasses binding, labeling, or catalyzing an enzymatic reaction. A "biological molecule" is any molecule which is found in a cell or within the body of an organism.

As used herein, "molecular procedure" refers to contact with a test reagent or molecular probe such as an antibody, nucleic acid probe, enzyme, chromagen, label, buffer, changes of temperature and the like.

As used herein, the term, "in communication with" refers to the ability of a system or component of a system to receive input data from another system or component of a system and to provide an output in response to the input data. "Output" may be in the form of data or may be in the form of an action taken by the system or component of the system.

As used herein, the term "provide" means to furnish, supply, or to make available.

As defined herein, the term "information relating to" is information which summarizes, reports, provides an account of, and/or communicates particular facts, and in some embodiments, includes information as to how facts were obtained and/or analyzed.

As used herein, the term "information about a patient" refers to any information known about the individual (a human or non-human animal) from whom a tissue sample was obtained. The term "patient" does not necessarily imply that the individual has ever been hospitalized or received medical treatment prior to obtaining a tissue sample. The term "patient information" includes, but is not limited to, age, sex, weight, height, ethnic background, occupation, environment, family medical background, the patient's own medical history (e.g., information pertaining to prior diseases, diagnostic and prognostic test results, drug exposure or exposure to other therapeutic agents, responses to drug exposure or exposure to other therapeutic agents, results of treatment regimens, their success, or failure, history of alcoholism, drug or tobacco use, cause of death, and the like). The term "patient information" refers to information about a single individual; information from multiple patients provides "demographic information," defined as statistical information relating to populations of patients, organized by geographic area or other selection criteria, and/or "epidemiological information," defined as information relating to the incidence of disease in populations.

As used herein, the term "tissue information" includes information relating to the expression of biological characteristics of a tissue as well as information about the source of the tissue (i.e., tissue information includes patient information).

As defined herein, a database is a collection of information or facts organized according to a data model which determines whether the data is ordered using linked files, hierarchically, according to relational tables, or according to some other model determined by the system operator. The organization scheme that the database uses is not critical to performing the invention, so long as information within the database is accessible to the user through an information management system. Data in the database are stored in a format consistent with an interpretation based on definitions established by the system operator (i.e., the system operator determines the fields which are used to define patient information, molecular profiling information, or another type of information category).

As defined herein, "a system operator" is an individual who controls access to the database.

As used herein, the term "information management system" refers to a system which comprises a plurality of functions for accessing and managing information within the database. Minimally, an information management system according to the invention comprises a search function, for locating information within the database and for displaying a least a portion of this information to a user, and a relationship determining function, for identifying relationships between information or facts stored in the database.

As defined herein, an "interface" or "user interface" or "graphical user interface" is a display (comprising text and/or graphical information) displayed by the screen or monitor of a user device connectable to the network which enables a user to interact with the database and information management system according to the invention.

Frozen Tissue Microarrayer Device

Figure 1A:
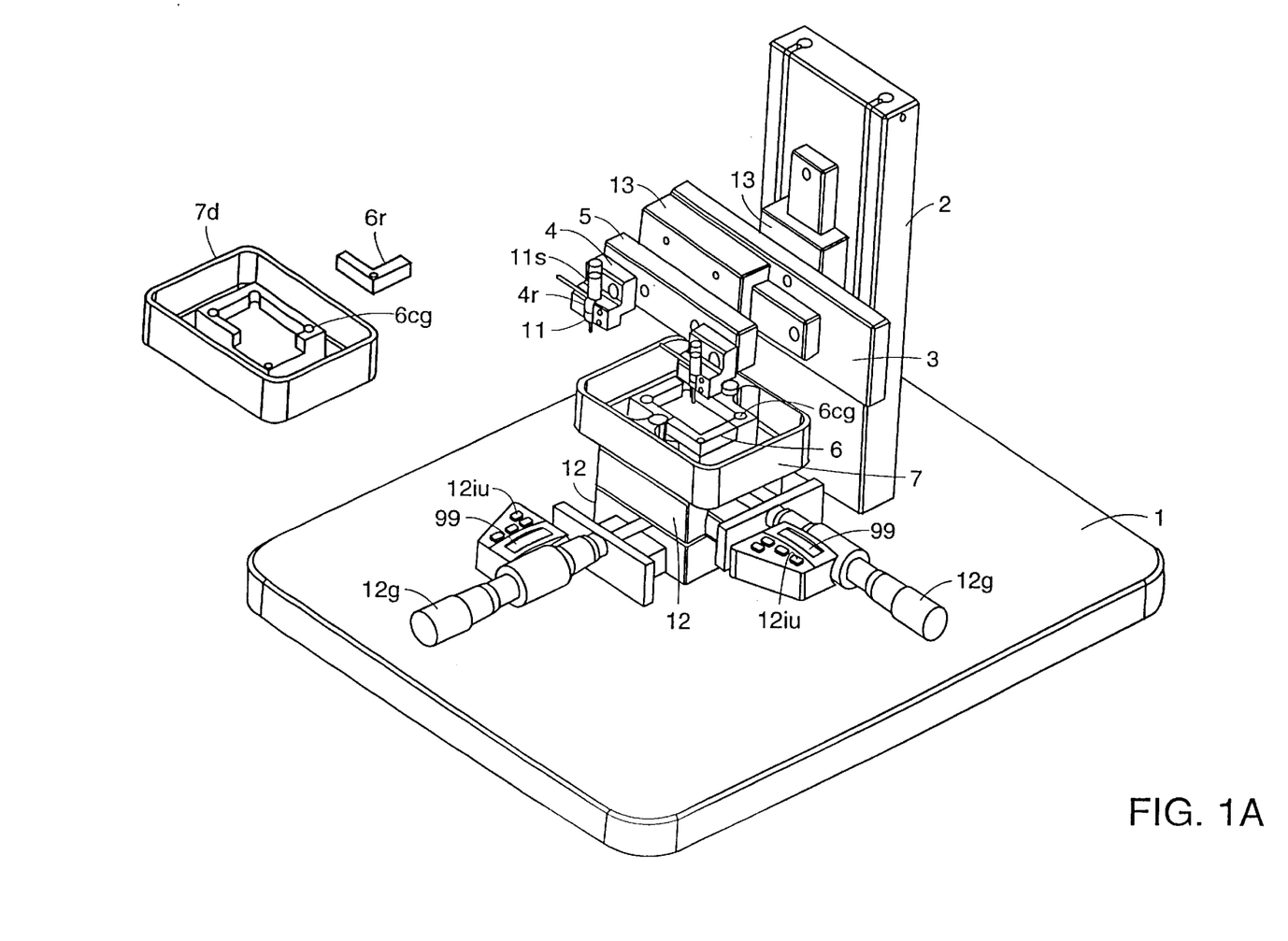
FIG. 1A, for example, shows a perspective view of a microarrayer device according to one embodiment of the invention.
Figure 1B:
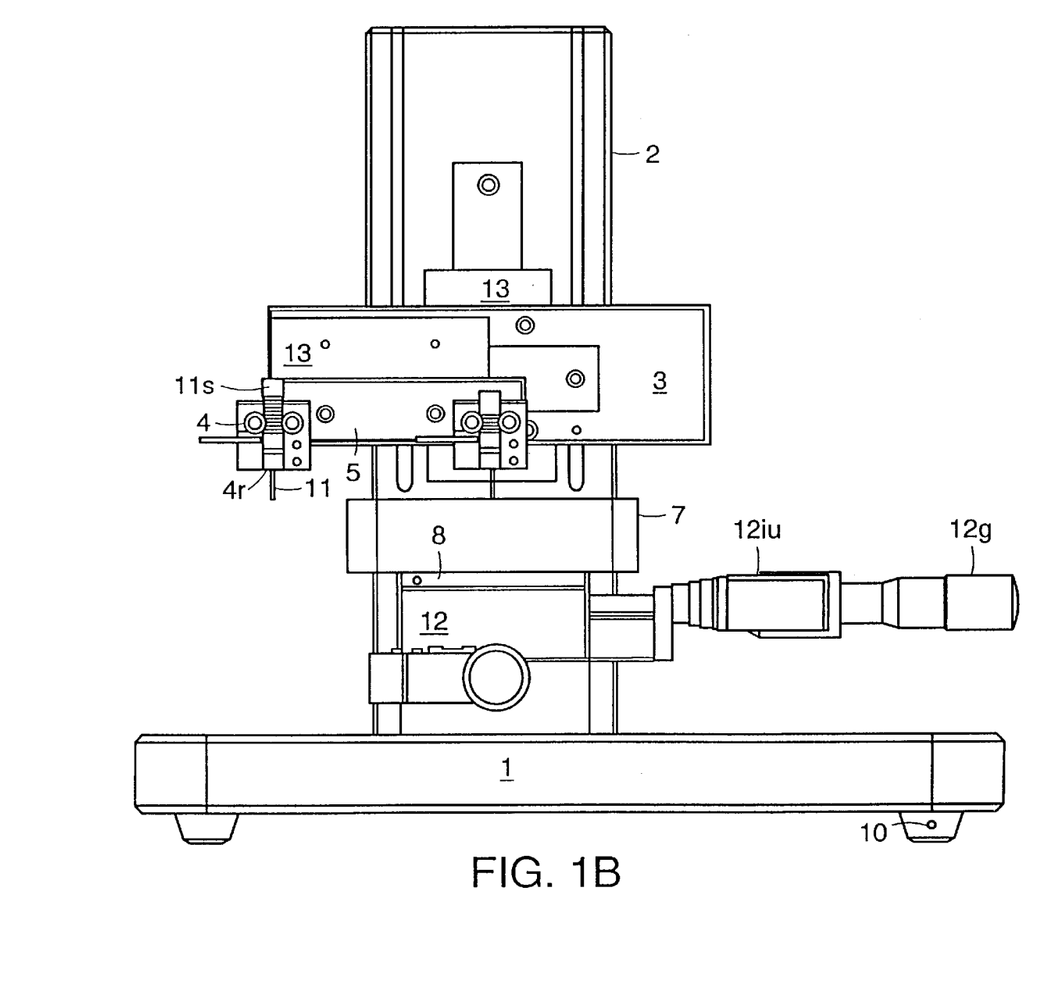
FIG. 1B shows a side view of the device shown in FIG. 1A with exemplary dimensions.
Figure 1C:
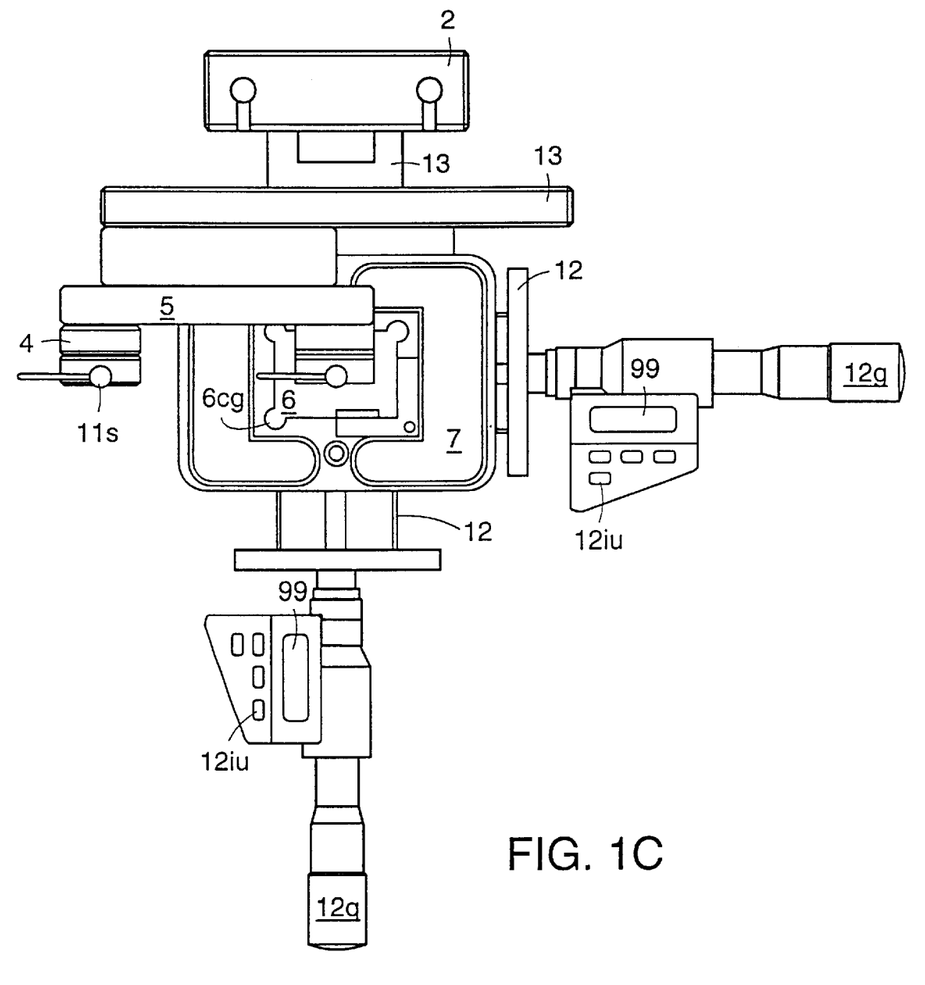
FIG. 1C shows a view looking down from the top of the device of FIG. 1A.

In one embodiment, as shown in FIG. 1A, for example, the frozen tissue microarrayer device comprises at least one platform 12 moveable in an x or y direction relative to a fixed horizontal surface 1 and a cooling chamber 7 for receiving at least one frozen material (e.g., such as a frozen tissue sample or a frozen embedding matrix) and for maintaining the frozen material in a frozen condition. In one embodiment, the cooling chamber 7 is moveable with the platform 12, such that when the platform 12 moves in an x-direction, the cooling chamber 12 also moves in an x-direction and when the platform moves in a y-direction, the cooling chamber 7 moves in a y-direction.

Figure 2A:
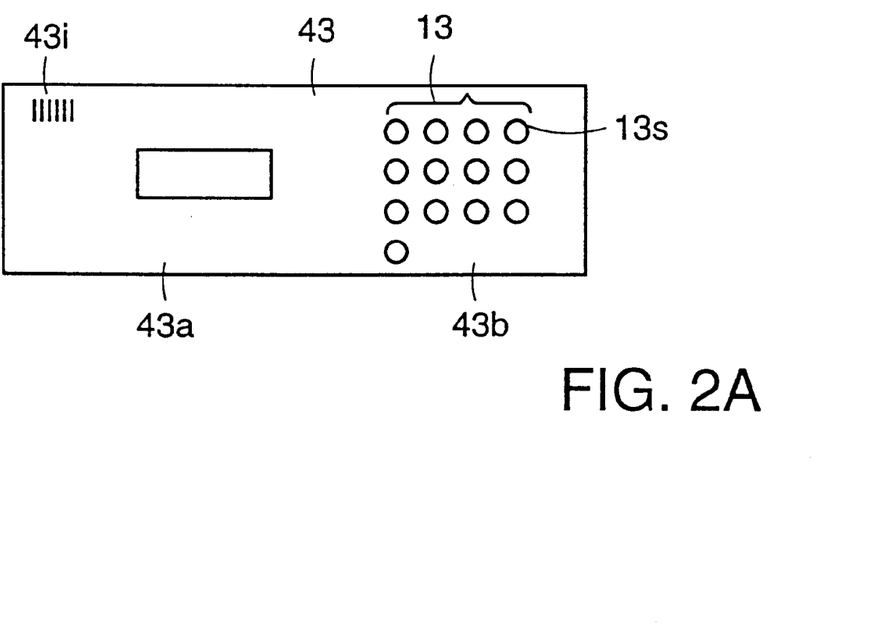
FIG. 2A shows a microarray generated according to an embodiment of the invention.

The cooling chamber 7 may be cooled in a variety of ways, e.g., by providing the cooling chamber 7 with a source of cold water (e.g., water cooled to 1° C. to 4° C.), a mixture of cold water and ice, or compressed air. In one embodiment, the cooling chamber 7 comprises sealed tubing configured to form a jacket of cooling fluid (e.g., water or air) around a block of frozen material. In one embodiment, an insulator sheet 8 (shown in FIG. 2) is placed between the platform 12 and cooling chamber 7, to minimize heat dissipation from the cooling chamber or heat conduction from the platform 12. In one embodiment, the cooling chamber 7 further comprises a retaining chamber 6 for retaining at least one block of frozen material. The retaining chamber 6 is preferably made of an insulating material for maintaining a temperature of from 0° C. to 4° C. or below. In some embodiments, the retaining chamber 6 is surrounded by cold water, a mixture of ice and water, or cold air (e.g., from a compressed air source which communicates with the cooling chamber 7), or a jacket through which a cooling fluid circulates.

In one embodiment, shown in FIG. 1A, for example, one or more blocks fits snugly into the retaining chamber 6 with substantially no clearance space between the block(s) and the retaining chamber 6 walls. In this embodiment, the retaining chamber 6 comprises one or more corner grooves 6 cg, to provide a levering space for an instrument (e.g., a spatula) used to lift the embedding block from the retaining chamber. In another embodiment (not shown), there is clearance between the block material and the walls of the retaining chamber 6, and the retaining chamber 6 comprises one or more holders for holding block(s) of frozen material in place (not shown).

In still another embodiment, a section of the retaining chamber, 6r can be removed from the chamber, for ease of grasping the block.

The device further accommodates at least one coring needle 11 comprising a cutting edge for cutting frozen material and a lumen for receiving a core of the cut frozen material. In one embodiment, the coring needle 11 is used to cut a core of embedded frozen tissue from a block of embedding matrix (e.g., a donor block). The same or a different coring needle 11 is used to cut a core of frozen embedding matrix from a block of an embedding matrix (e.g., a recipient block) which is used to form one or more microarrays, leaving a hole of approximately the same size or a size slightly smaller than the core of tissue. The core of frozen tissue is then placed in the hole previously filled by the core of embedding matrix. The process is repeated multiple times until a recipient block comprising a plurality of tissue cores is generated, i.e., a microarray block is formed.

The shape of the coring needle 11 may vary. In one embodiment, the lumen of the coring needle 11 forms a cylindrical space (e.g., for forming a cylindrical core of tissue). However, other shapes are included within the scope of the invention. In one embodiment, the cross-section perpendicular to the longitudinal axis of the coring needle 11 is any of: circular, rectangular, polygonal, oval, square, trapezoidal shaped, and the like. Preferably, the coring needle 11 has a uniform cross-section. The size of the core of frozen material can also vary. In one embodiment, a core of frozen material of 1–10 mm in length can be obtained using the coring needle 11. In one embodiment, the diameter of the core thus obtained ranges from 0.4 to 10.0 mm, and preferably about 0.3–2.0 mm.

In one embodiment of the invention, the microarrayer device comprises a first and second coring needle 11, the first coring needle 11 (donor coring needle) dedicated to coring tissue samples, the second coring needle 11 (recipient coring needle) dedicated to coring holes in the recipient block. In this embodiment, preferably the donor coring needle 11 is slightly larger than the recipient coring needle 11 (e.g., the second coring needle 11 would be able to slidably fit within the first coring needle 11). The lumens of the coring needles 11 are sized such that a tissue sample obtained from a donor block snugly fits in a hole created in the recipient block.

The device further comprises a positioning element 4 for positioning the at least one coring needle 11 over a donor block or recipient block. In one embodiment of the invention, the positioning element 4 comprises a recess 4r for receiving a coring needle 11 and a clip (not shown) for securing the coring needle 11 within the recess 4r. In one embodiment, the clip is a spring clip, which is held in place on the positioning element 4 by means of a screw. In another embodiment, the coring needle 11 comprises a circumferential groove which mates with a ridge, tab, or pin (not shown) in the walls of the recess 4r, while still allowing the coring needle 11 to rotate. This embodiment constrains horizontal motion of the coring needle 11 within the positioning element 4, but allows the coring needle 11 to be moved clockwise and counterclockwise to disengage from a block of frozen tissue into which it has cored.

In one embodiment, the positioning element 4 is positioned randomly over a tissue sample. However, in a preferred embodiment, a section of a donor block which is representative of tissue embedded in the entire donor block is examined (e.g., under a microscope) and the coordinates of a tissue site for inclusion within a microarray are determined (e.g., using a micrometer or gridlines on a microscope slide on which the tissue sample is placed). In one embodiment, the coordinates are selected by selecting desired morphological features in the tissue sample (e.g., selecting coordinates which include an area of abnormal cell proliferation).

However, in another embodiment, a slide comprising the representative tissue sample is reacted with molecular probe (s) to identify the expression of at least one molecular marker (e.g., a nucleic acid, MRNA, protein, modified form of a protein, and the like), and coordinates are selected which express, or do not express, the marker. In one embodiment, the marker is a heterogeneously expressed biomolecule (e.g., expressed in fewer than 80% of cells in a given tissue type) and coordinates are selected which include at least one cell expressing the marker. In another embodiment, a tissue sample is selected which comprises cells which do express the heterogeneously expressed biomolecule as well as cells which do not express the molecule. In a further embodiment, a tissue sample is selected which comprises both normally and abnormally proliferating cells (e.g., non-cancerous and cancerous cells).

In one embodiment, after suitable coordinates are identified, the donor block is placed in the retaining chamber 6 for coring, is cored, and removed. The recipient block is then placed in the chamber, is cored, and receives the core of tissue sample obtained from the donor block. However, in another embodiment, the recipient block is pre-cored and comprises at least one hole for receiving a core of tissue sample.

In a further embodiment, the retaining chamber 6 is designed to accommodate at least two blocks of frozen materials (e.g., such as a donor and a recipient block), eliminating the need to remove a donor block before coring the recipient block. In still a further embodiment, a plurality of positioning elements 4 is provided to accommodate a plurality of coring needles. In one embodiment, the plurality of positioning elements are coupled to a single holder arm 4, such that movement of the positioning elements 4 in at least an x-direction is coordinated.

In one embodiment, a coring needle 11 is centered over appropriate coordinates of a donor block as determined by evaluating a representative tissue section from the donor block using a gridded slide. A template comprising gridlines identical to those on the slide is placed on the donor block, using an orienting mark on the donor block to position the template. In one embodiment, the template is the slide that was used to identify desired coordinates. The retaining chamber 6 comprising the frozen material is moved to center the appropriate coordinates of the donor block under the coring needle 11, e.g., by centering the appropriate template gridlines under the coring needle 11. The retaining chamber 6 can be moved by moving any of the cooling chamber 7, platform(s) 12, or the chamber 6 itself. Alternatively, or additionally, the positioning element 5 comprising the coring needle is moved to center the appropriate coordinates of the donor block under the coring needle 11. The template is then removed, and the coring process is initiated. In one embodiment, the device is provided with one or more ocular elements, to allow the user to better visualize features on the template (or slide) when moving the retaining chamber 6 and/or positioning element 4.

Movement of either the retaining chamber 6 or positioning element 4 may be controlled by providing one or more motorized elements (not shown) in communication with the retaining chamber 6 and/or positioning element 4. In one embodiment, shown in FIG. 1A, for example, movement of both the positioning element 4 and the retaining chamber 6 is controllable by the user either directly or through a processor 99 in communication with the motor(s).

In one embodiment, the movement of the retaining chamber 6 is coupled to that of the cooling chamber 7 which is turn is coupled to movement of at least one platform 12. The movement of the platform 12 can be controlled manually, e.g., by using a grasping element 12g (e.g., such as a joystick) coupled the platform 12, or can be mechanically controlled, e.g., by providing a motor in communication with the platform 12. In one embodiment, an x-direction platform 12 in communication with an x-direction motor is provided for controlling movement of the cooling chamber 7 in an x-direction, and a y-direction platform 12 in communication with a y-direction motor is provided for controlling movement of the cooling chamber 7 in a y-direction. By providing both platforms, the cooling chamber 7 is able to move in both an x- and y-direction.

In one embodiment of the invention, the x- and/or y-direction motors are servo motors which are responsive to signals from a processor (not shown). In another embodiment of the invention, the processor is in communication with at least one input unit 12iu into which the user can input desired x- or y-coordinates respectively. Servo motors and control devices are well known in the art and are described, for example, in U.S. Pat. Nos. 5,194,793 and 5,194,790, the entireties of which are incorporated by reference herein.

Other types of motors, such as drive motors and stepper motors, can also be used (see, as discussed in U.S. Pat. Nos. 5,194,790, 5,139,005, and 5,103,338, the entireties of which are incorporated by reference herein).

In the embodiment shown in FIG. 1A, for example, movement of the positioning element 4 is also controllable by a user, permitting a further means to precisely position an at least one coring needle 11 relative to a frozen tissue sample or block of embedding matrix. In this embodiment, the positioning element 4 is coupled to a x-direction slide 13 which moves in an x-direction upon receiving a mechanical force, either from a user (e.g., by pushing on the slide 13), or from a motorized element (not shown) which is coupled to x-direction slide plate 3. In a further embodiment (not shown), an additional degree of freedom of motion is afforded by pivotally connecting the positioning element 4 to the x-direction slide 13. It should be obvious to those of skill in the art, that any of a number of slide elements may be provided, which may be pivotally coupled or fixedly coupled to one or more other slide elements and/or plates.

In the embodiment shown in FIG. 1A, there are two positioning elements 4 and the movement of both elements is coordinated by coupling both positioning elements 4 to a single positioning element holder 5. However, in another embodiment, the ability to move independently can be afforded to each positioning element 4, for example, by pivotally coupling each positioning element 4 to the positioning element holder 5.

The positioning element(s) 4 can be fixed in place once a desired position is reached by providing one or more screw elements (not shown) for screwing one or more slide elements at a given position and/or by providing one or more screw elements for screwing the positioning elements 4 themselves (e.g., such as in the embodiment where these are able to pivot about the positionery element holder 5).

Once a donor block and/or recipient block is satisfactorily positioned relative to at least one coring needle 11, the coring process can be initiated. In one embodiment, shown in FIG. 1A, coring of a block of frozen material which is secured in the retaining chamber 6 is controlled by coupling one face of an x-direction vertical slide 13 (a slide that can move both in an x and z direction) to positioning element holder 5 and another face to a vertical slide plate 2. In this embodiment, vertical translation of the vertical slide 13 (e.g., in a z-direction), in turn, moves the positioning element 4 in a z-direction. When the positioning element 4 is directed downwards, a linear force is exerted against the cutting edge of the coring needle 11 secured in the recess 4r of the positioning element 4. This force translates into a cutting action by the coring needle 11, driving a core of frozen material (e.g., tissue or embedding matrix) into the lumen of the coring needle 11. Vertical movement upwards pulls the coring needle 11 with its core of frozen material out of the frozen block; as the coring needle 11 is moved upwards, its ability to rotate clockwise and/or counterclockwise also aids in disengaging it from the block of frozen material.

In one embodiment, where a single coring needle 11 is provided and donor and recipient blocks are placed sequentially in the retaining chamber 6, after placement of a donor block and coring by the coring needle 11, the coring needle 11 with its core of tissue sample is moved via the positioning element 4 to a "parking position" (e.g., by pushing the holder 5 in an x-direction or z-direction away from the retaining chamber, or by pivoting the positioning element 4 about a pivot point on the holder 5, swinging the positioning element away from the donor block). The donor block is then removed from the retaining chamber 6, and a recipient block (which has been pre-cored) is placed in the chamber 6. The positioning element 4 is positioned over an appropriate hole in the recipient block and the core of tissue is pushed or ejected from the coring needle 11 into the recipient block. The positioning element 4 is again moved aside while the recipient block is removed and a new donor block placed in the retaining chamber.

In another embodiment, a donor block is placed on a removable bridge (not shown) on top of a pre-cored recipient block, and when the donor tissue is obtained, the bridge with the donor block is displaced (e.g., manually or by coupling the bridge to a swing arm), making the recipient block accessible to the coring needle 11. The coring needle 11 is then moved vertically downward to just above a hole in the recipient block, the recipient block having been previously properly positioned relative to the position of the coring needle 11. The tissue core is then expelled from the coring needle 11 into the hole in the recipient block without having to take time to position the recipient block.

In a preferred embodiment, shown in FIG. 1A, for example, the device provides at least two coring needles 11, each secured in a different positioning element 4. In this embodiment, a first coring needle 11 is dedicated for coring donor blocks, while a second coring needle 11 is dedicated for coring recipient blocks. The retaining chamber 6 is sized to receive both a donor block and recipient block simultaneously.

In still a further embodiment, a donor block is kept cooled within an insulated cooling chamber 7d outside of the device while the recipient block is processed in a cooling chamber 7. The cooling chamber 7 can then be removed from the device while cooling chamber 7d is seated on platform 12 for processing the donor block.

In one embodiment, the movement of both the first and second coring needle 11 is coordinated. For example, in one embodiment, as shown in FIG. 1A, for example, both the first and second positioning elements are coupled to a single x-direction slide 13, such that each positioning element 4 moves in identical increments. In one embodiment, when the first coring needle 11 (the donor coring needle 11) moves to a first position over selected coordinates on the donor block, the second coring needle 11 moves to a second position over identical coordinates on the recipient block. In this embodiment, while the first coring needle 11 cores a tissue sample from the donor block the second coring needle 11 is coring a core of embedding matrix from the recipient block.

In one embodiment, a donor coring needle 11 comprising a core of donor tissue is moved from a first position over a donor block to a second position over a recipient block, e.g., by sliding the holder 5 in an x-direction, or by providing a slide rail on the holder 5, on which the positioning element 4 can itself be slid. The recipient coring needle 11 comprising a core of embedding matrix is then pushed away from the recipient block by sliding and/or pivoting the positioning element 4 securing the recipient coring needle 11. In this embodiment, the core of donor tissue is ejected from the donor coring needle 11 into the hole in the recipient block created by the recipient coring needle 11 while the core of embedding matrix is removed from the recipient coring needle 11. A new donor block is then placed in the retaining chamber 6, and the first and second coring needle 11's are returned to the first and second position, respectively (i.e., positioning the first coring needle 11 over the new donor block and the second coring needle 11 back over the recipient block), and the process is repeated.

In another embodiment of the invention, the retaining chamber 6 is sized to accommodate a waste chamber (not shown) at a third position within the retaining chamber 6. In this embodiment, rather than being placed in a parking position when the first coring needle 11 is positioned over the recipient block, the second coring needle 11 is positioned over the waste chamber and the core of embedding matrix within the second coring needle 11 is deposited in the waste chamber as the first coring needle 11 deposits the core of tissue sample in the recipient block.

In further embodiments of the invention, more than two coring needles 11 (and more than two positioning elements 4) are provided. In one embodiment, a first, second, and third coring needle 11 are provided, the first being slightly larger than the second, the second being slightly larger than the third. In this embodiment, the user can choose to use the first coring needle 11 as the donor needle and the second coring needle 11 as the recipient needle, or can choose to use the second coring needle 11 as the donor needle and the third coring needle 11 as the recipient needle. Thus, the user can create microarray blocks comprising different-sized tissue cores using a single microarrayer device according to the invention. In one embodiment, a microarray is generated comprising a plurality of tissues, each tissue having any of a plurality of selectable sizes. In another embodiment, a single microarray block is generated which comprises differently sized cores.

Placement of blocks within, and removal from, the retaining chamber 6 can be mediated in a variety of ways. In one embodiment, a block may be gently pried from the retaining chamber 6, e.g., by using a spatula to lift the edges of the block. In another embodiment, the bottom of the retaining chamber 6 is controllably magnetized (e.g., by a processor in communication with the microarrayer), and a magnetic element is placed on the bottom of the frozen block (e.g., via an adhesive backing). When a frozen block is to be removed, the magnetic field is turned off, thereby releasing the block. In still another embodiment of the invention, the base of the retaining chamber 6 comprises a conveyer belt, or movable platform and blocks are mechanically moved from one position to another. In still another embodiment, this process is controlled by a processor in communication with the microarrayer device.

In one embodiment, the coring process is facilitated by the use of one or more stylets 11s to push frozen tissue or embedding matrix out of the lumen of the coring needle 11. In one embodiment, the coring needle 11 is in communication with a stylet 11s which can be slideably moved in and out of the lumen of the coring needle 11. The movement of the stylet 11s can be manually controlled or powered by mechanical (e.g., wind-up), electrical, electromagnetic, pneumatic or hydraulic mechanisms. In one embodiment, the movement of the stylet 11s is controlled by a stylet driver (not shown) which is in communication with the stylet 11s and which responds to signals from a processor.

A variety of stylets 11s's can be used. In one embodiment, the stylet 11s comprises a stylet needle having a pushing surface and a connecting end for connecting to a stylet body. The stylet needle is stabilized within the stylet body by a stylet tube into which the stylet needle can slideably fit. In one embodiment, the stylet body comprises two separable units, a stylet base and a stylet cap, each separated from each other by a resilient element. When linear force is provided to the stylet needle (e.g., by pushing on the stylet cap and/or by downward movement of the stylet controlled by the stylet driver), the pushing surface of the stylet needle contacts frozen tissue and/or embedding matrix within the lumen of the coring needle 11 and ejects the material from the coring needle (into the hole of a recipient block in the case of a tissue sample, or into a waste receptacle, in the case of embedding matrix from the recipient block). The release of force on the stylet cap creates a recoil force which is amplified through the resilient element, driving the stylet upwards again.

In a preferred embodiment, a stylet is used which is resistant to the impact of repetitively contacting frozen tissue or frozen embedding media. Still more preferably, a stylet is used which can be reused at least 100 times and is disposable. A suitable stylet which has these properties is described in U.S. application Ser. No. 09/779,187, filed Feb. 8, 2001, the entirety of which is incorporated by reference herein. Additional stylets are described in U.S. Pat. No. 6,103,518, the entirety of which is incorporated by reference herein.

In one embodiment, coordination of the movement of the stylet 11s with the movement of the coring needle 11 is used to control the depth of coring. In a manual process, contacting of the blocks of frozen material by the coring needle 11 is detected visually and/or by touch. However, in one embodiment, where the microarrayer device operates automatically or semi-automatically, a processor is provided in communication with a detector which is placed in proximity to the retaining chamber 6 (not shown). The detector is capable of detecting optical information relating to the position of the surface of block(s) positioned beneath the coring needle(s) 11. The detector communicates this information in the form of signals to the processor, which in turn communicates with one or more motors coupled to the positioning element 4 and/or slider elements (e.g., 13) of the device.

In one embodiment, the stylet needle of the stylet 11s protrudes a fixed and known distance from the bottom of the cutting edge of the coring needle 11, for example when the lumen of the coring needle 11 is empty. The stylet 11s, which is slideable in the lumen of the coring needle 11, contacts the block but does not penetrate. When the coring needle moves downwards (e.g., through the action of a z-direction slide), the stylet 11s slides upwards within the lumen of the coring needle 11, pushed upwards by the core of frozen material received by the lumen of the coring needle. Upon receiving an ejection signal (e.g., from a stylet driver in communication with a processor) (not shown), the stylet needle moves downwards through the lumen of the coring needle to eject the core of frozen material.

In one embodiment of the invention, motion of the stylet 11s is detected by a detector (such as one responsive to optical or electromagnetic signals from the stylet) and signals from the detector are routed to a processor which in turn sends signals to one or a plurality of slide elements to which the stylet driver is coupled, thereby controlling the motion of the stylet. Additional methods of monitoring and controlling the movement of a stylet relative to a coring needle are described in U.S. Pat. No. 6,103,518, the entirety of which is incorporated by reference herein.

Forming Tissue Microarrays for the Microarray Block

Once the desired number of tissue samples have been removed from donor block(s) and placed in a recipient block, the recipient block becomes a microarray block from which a plurality of microarrays can be generated. In one embodiment, microarrays are generated by slicing the microarray block into a plurality of sections, for example by using a microtome (see, e.g., as described in U.S. Pat. Nos. 664,118; 2,292,973; 2,680,992; 3,420,13; 3,440,913; 3,496, 819; 3,799,029; and 3,975,977, the entireties of which are incorporated herein by reference).

Figure 2B:
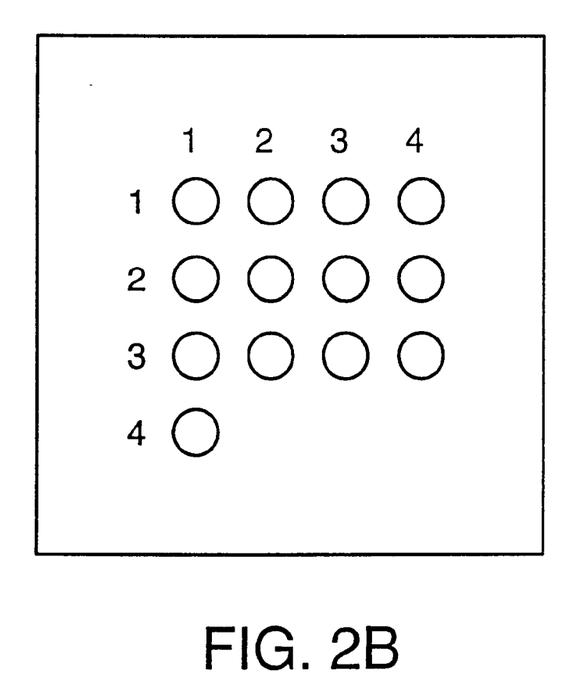
FIG. 2B shows a microarray locator according to one embodiment.

As shown in FIGS. 2A and B, microarrays 13 according to the invention comprise a plurality of sublocations 13s, each sublocation comprising a tissue sample having at least one known biological characteristic (e.g., such as tissue type). In one embodiment, the tissue sample at at least one sublocation 13s has morphological features substantially intact which can be at least viewed under a microscope to distinguish subcellular features (e.g., such as a nucleus, an intact cell membrane, organelles, and/or other cytological features), i.e., the tissue is not lysed.

In one embodiment, sections of 4–7 µm in thickness are obtained from the microarray block by sectioning and one or more sections are placed on a substrate to facilitate handling during one or more molecular procedures. In one embodiment, a molecular procedure comprises a plurality of hybridizations, incubations, fixation steps, changes of temperature (from −4° C. to 100° C.), exposures to solvents, and/or wash steps.

In one embodiment of the invention, the microarray substrate 43 is solvent resistant. In another embodiment of the invention, the substrate 43 is transparent. In still another embodiment of the invention, the microarray substrate 43 comprises any of: glass; quartz; fused silica; or other non-porous substrate, plastic, such as polyolefin, polyamide, polyacarylamide, polyester, polyacrylic ester, polycarbonate, polytetrafluoroethylene, polyvinyl acetate, and a plastic composition containing fillers (such as glass fillers), extenders, stabilizers, and/or antioxidants; celluloid, cellophane or urea formaldehyde resins, or other synthetic resins such as cellulose acetate ethylcellulose, or other transparent polymers.

In one embodiment, the microarray substrate 43 is rigid; however, in another embodiment, the substrate 43 is semi-rigid or flexible (e.g., a flexible plastic comprising polycarbonate, cellular acetate, polyvinyl chloride, and the like). In a further embodiment, the substrate 43 is optically opaque and substantially non-fluorescent. Nylon or nitrocellulose membranes can also be used as substrates and include materials such as polycarbonate, polyvinylidene fluoride (PVDF), polysulfone, mixed esters of cellulose and nitrocellulose, and the like.

In one embodiment of the invention, each sublocation 13s of the microarray 13 corresponds to a sublocation 13s on the substrate 43 and each substrate 43 sublocation comprises a tissue stably associated therewith (e.g., able to retain its position relative to another sublocation after exposure to at least one molecular procedure). The size and shape of the substrate 43 may generally be varied. However, preferably, the substrate 43 fits entirely on the stage of a microscope. In one embodiment, the substrate 43 is planar. In one embodiment of the invention, the microarray substrate 43 is 1 inch by 3 inches, 77×50 mm, or 22×50 mm. In another embodiment of the invention, the microarray substrate 43 is at least 10–200 mm×10–200 mm.

In another embodiment of the invention, shown in FIG. 2A, the substrate 43 is a "profile array substrate" designed to accommodate a control tissue microarray and a test tissue or cell sample for comparison with the control tissue microarray. In this embodiment, the substrate 43 comprises a first location 43a and a second location 43b. The first location 43a is for placing a test tissue sample, while the second sublocation 43b comprises the microarray 13. This profile microarray substrate 43 allows testing of a test tissue sample to be done simultaneously with the testing of tissue samples on the microarray 13 having at least one known biological characteristic allowing for a side by side comparison of biological characteristics expressed in the test sample with the characteristics of the tissues in the microarray 13. Profile microarray substrates 43 are disclosed in U.S.

Provisional Application Serial No. 60/234,493, filed Sep. 22, 2000, the entirety of which is incorporated by reference herein.

Addressing the Microarray

While the order of sublocations 13s on the microarray 13 is not critical, in a preferred embodiment, the sublocations 13s of the microarray 13 are positioned in a regular repeating pattern (e.g., rows and columns) such that each sublocation 13s can be assigned coordinates relating to its position on the microarray 13. For example, a sublocation 13s in row 1, column 1, would be assigned the coordinates (1,1), while a sublocation 13s in row 1, column 5 would be assigned coordinates (1,5). In this embodiment of the invention, coordinates of sublocations on the microarray correspond to the coordinates of the holes in the recipient block which became the microarray block.

In one embodiment, shown in FIG. 2B a microarray locator 45 is provided to enable the user to easily determine the coordinates of a sublocation 13s of interest on the microarray 13. The microarray locator 45 is a template having a plurality of shapes 45s, each shape 45s corresponding to the shape of each sublocation 13s in the microarray 13, and maintaining the same relationships as each sublocation 13s on the microarray 13 (see FIG. 6B, for example). The microarray locator 45 is itself marked by coordinates 46, allowing the user identify the coordinates of sublocation (s) 13s on the microarray 13 by overlaying the microarray locator 45 on top of the microarray 13 and aligning the shapes 45s on the template with the sublocations 13s on the microarray 13. In one embodiment of the invention, the microarray locator 45 is a transparent sheet (e.g., plastic, acetate, and the like). In another embodiment of the invention, the microarray locator 45 is a sheet comprising a plurality of holes, each hole corresponding in shape and location to each sublocation 13s on the microarray 13.

Figure 3:
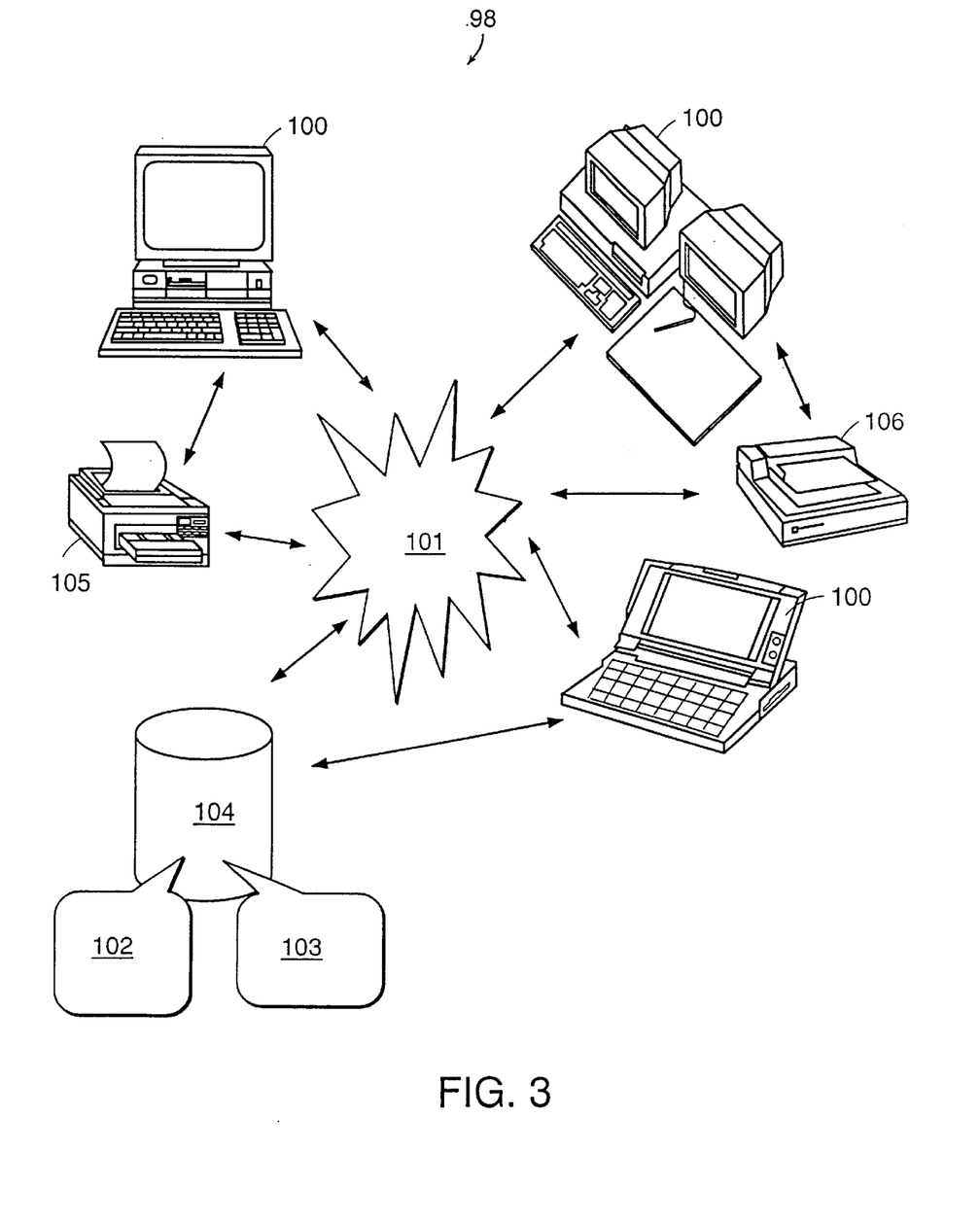
FIG. 3 shows a tissue information system according to one embodiment of the invention.
Figure 4:
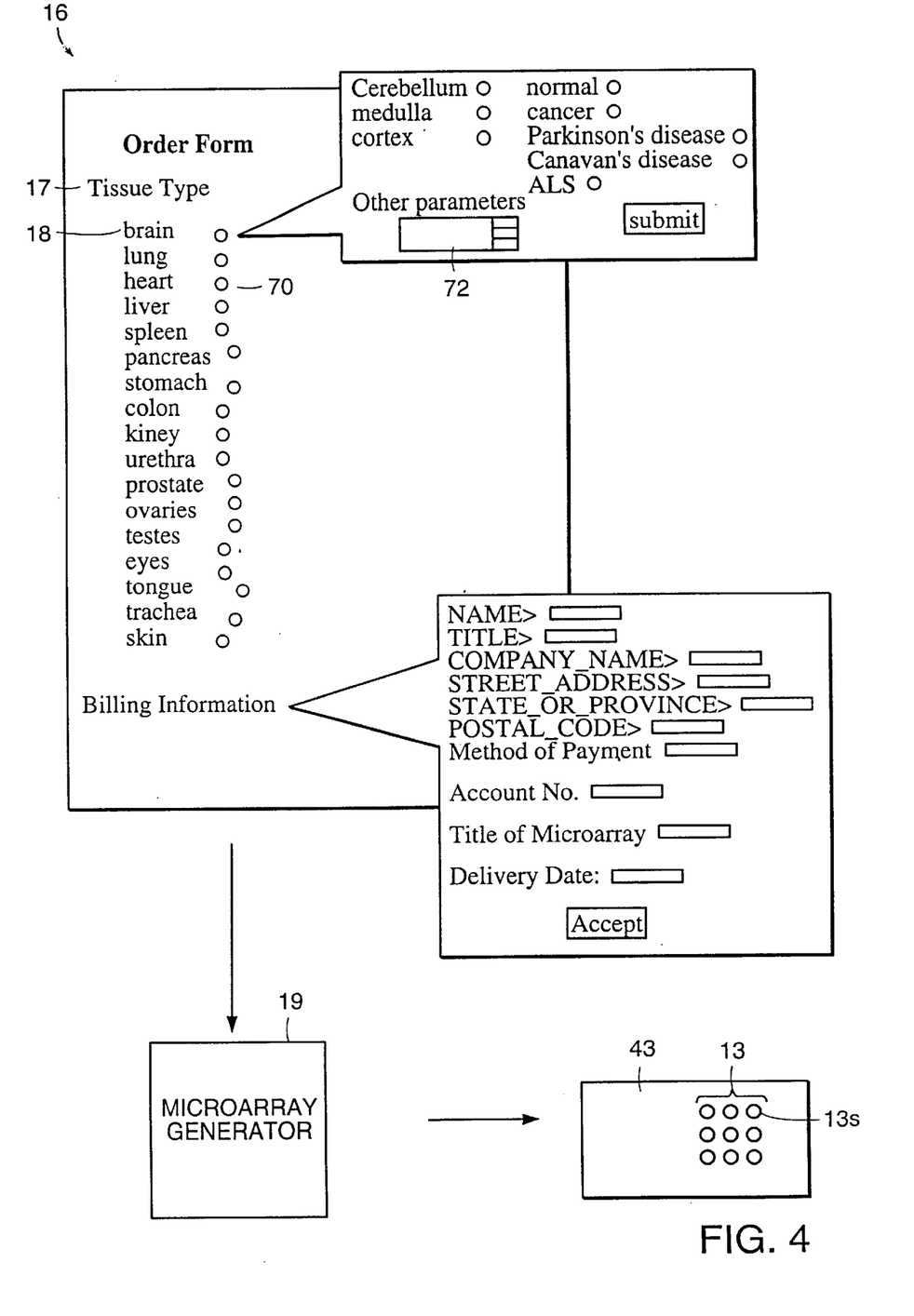
FIG. 4 shows a schematic diagram of a system for ordering customized tissue microarrays over the network.

In another embodiment of the invention, substrate 43 itself comprises encoded addressing information at each sublocation 13s on the substrate 43, so that the coordinates of a particular tissue on the microarray 13 can be electronically and remotely determined. For example, in one embodiment of the invention, the substrate 43 is printed on an electrically conductive surface comprising a plurality of address lines. In another embodiment, holes are incorporated into the substrate 43 which may be detected by mechanical or optical means; the holes providing position information (e.g., coordinates) that can be related to information about the tissues at particular sublocations 13s which is stored in an information retrieval database described further below (see FIG. 3). Magnetic or other devices can also be incorporated into the substrate 43 to provide a means of identifying the coordinates of selected sublocations 13s on the microarray 13.

In a further embodiment of the invention, the substrate 43 comprises a location for placing an identifier 43i (e.g., a wax pencil or crayon mark, an etched mark, a label, a bar code, a microchip, or other means for transmitting electromagnetic signals, a radiofrequency transmitter, and the like). In one embodiment, the means for transmitting electromagnetic signals communicates with a processor 47 which comprises, or can access, stored information relating to the identity and address of sublocations 13s on the microarray 13, and/or information regarding the individual from whom the tissue was obtained, e.g., such as prognosis, diagnosis, medical history of the patient, family medical history, drug treatment, age of death and cause of death, and the like. In still a further embodiment, the identifier 43i further includes a means to identify the position in the microarray block from which the section forming the microarray was generated (e.g., the section number, where a plurality of serial sections have been obtained).

Sources of Tissue

In one embodiment, donor blocks are used which comprises tissues from cadavers or patients who have recently died, and/or from surgical specimens, pathology specimens, or which represent "clinical waste" tissue that would normally be discarded from other procedures. In addition to tissue sections, microarrays 13 can also include cells from bodily fluids such as serum, leukophoresis products, and pleural effusions, or cells from cell culture lines (either primary or continuous cell lines).

In one embodiment of the invention, a microarray 13 comprises representative tissues from an organism. In one embodiment, the microarray 13 encompasses the "whole body" of one or a plurality of individuals. In another embodiment of the invention, the microarray 13 is a reflection of a plurality of traits representing a particular patient demographic group of interest, e.g., overweight smokers, diabetics with peripheral vascular disease, individuals having a particular predisposition to disease (e.g., to sickle cell anemia, Tay Sachs, severe combined immunodeficiency, and the like).

In another embodiment of the invention, a microarray 13 is provided comprising a plurality of sublocations 13s which represent different stages of a cell proliferation disorder, such as cancer. In one embodiment, the microarray 13 includes metastases to tissues other than the primary cancer site. In still a further embodiment of the invention, the microarray 13 comprises normal tissues, preferably from the same patient from whom the abnormally proliferating tissue was derived. Staged oncology tissue microarrays 13 are described in U.S. Provisional Application Serial No. 60/236, 649, filed Sep. 29, 2000 (Attorney Docket No. 5568/1040), the entirety of which is incorporated by reference herein.

In another embodiment, at least one sublocation 13s comprises cells from a cell line of cancerous cells, either primary or continuous cell lines. Cell lines can be developed from isolated cancer cells and immortalized with oncogenic viruses (e.g., Epstein Barr Virus). Exemplary cell lines which can be used in this embodiment are described in U.S. Provisional Application Serial No. 60/236,649, the entirety of which is incorporated herein by reference.

In another embodiment of the invention, the microarray 13 comprises a plurality of sublocations 13s comprising cells from individuals sharing a trait in addition to cancer. In one embodiment of the invention, the trait shared is gender, age, a pathology, predisposition to a pathology, exposure to an infectious disease (e.g., HIV), kinship, death from the same illness, treatment with the same drug, exposure to chemotherapy or radiotherapy, exposure to hormone therapy, exposure to surgery, exposure to the same environmental condition (e.g., such as carcinogens, pollutants, asbestos, TCE, perchlorate, benzene, chloroform, nicotine and the like), the same genetic alteration or group of alterations, expression of the same gene or sets of genes, a disease predisposition, a psychiatric disorder, In another embodiment of the invention, at least one sublocation 13s comprises cells from an individual with an enhanced cancer susceptibility (e.g., a family history of cancer, a patient whose has had cancer previously, or an individual who is exposed to carcinogen(s)).

In one embodiment, the microarray 13 comprises at least one sublocation 13s comprising cancerous cells from a single patient and comprises a plurality of sublocations 13s comprising cells from other tissues and organs from the same patient. In a further embodiment of the invention, each sublocation 13s of the microarray comprises cells from different members of a pedigree sharing a family history of cancer (e.g., selected from the group consisting of siblings, twins, cousins, mothers, fathers, grandmothers, grandfathers, uncles, aunts, and the like). In another embodiment of the invention, this "pedigree microarray" comprises environment-matched controls (e.g., husbands, wives, adopted children, step-parents, and the like).

In a further embodiment of the invention, the microarray 13 comprises at least one sublocation 13s comprising tissue from an individual with a disease other than cancer, or in addition to cancer (e.g., including, but not limited to: a blood disorder, blood lipid disease, autoimmune disease, bone or joint disorder, a cardiovascular disorder, respiratory disease, endocrine disorder, immune disorder, infectious disease, muscle wasting and whole body wasting disorder, neurological disorders (including both the central nervous system and peripheral nervous system), skin disorder, kidney disease, scleroderma, stroke, hereditary hemorrhage telangiectasia, disorders associated with diabetes, hypertension, diabetes, manic depression, depression, borderline personality disorder, anxiety, schizophrenia, Gaucher disease, cystic fibrosis and sickle cell anemia, liver disease, pancreatic disease, eye, ear, nose and/or throat disease, diseases affecting the reproductive organs, gastrointestinal diseases, including diseases of the colon, diseases of the spleen, appendix, gall bladder, and the like). For further discussion of human diseases, see *Mendelian Inheritance in Man: A Catalog of Human Genes and Genetic Disorders* by Victor A. McKusick (12th Edition (3 volume set) June 1998, Johns Hopkins University Press, ISBN: 0801857422), the entirety of which is incorporated herein.

In one embodiment, sets of microarrays 13 are provided representing multiple individuals with approximately 30,000 tissue specimens covering at least 5, 10, 15, 20, 25, 30, 40, or 50, different disease categories, including, but not limited to, any of the disease categories identified above.

Although in a preferred embodiment of the invention the microarrays 13 comprise human tissues, in one embodiment of the invention, abnormally proliferating tissues from other organisms are arrayed. In one embodiment, the microarray 13 comprises tissues from non-human animals (e.g., mice) which have either spontaneously developed cancer or who have received transplants of tumor cells. In one embodiment, the microarray 13 comprises multiple tissues from such a non-human animal. In another embodiment of the invention, the microarray 13 comprises tissues from non-human animals which have spontaneously developed cancer or who have received transplants of tumor cells, and which have been treated with a cancer therapy (e.g., drugs, antibodies, protein therapies, gene therapies, antisense therapies, and the like).

In still a further embodiment of the invention, tissues from a non-human animal genetically engineered to over express or under express desired genes are provided. In one embodiment, a microarray 13 is provided comprising tissues from non-human animals expressing different doses of the same cell proliferation gene or tumor suppressor gene. In still a further embodiment, a microarray 13 is provided comprising a plurality of cell lines (normal and/or cancer cell lines) which have been genetically engineered to express cell proliferation genes or tumor suppressor genes or modified forms of such genes. In this embodiment, cells may stably or transiently transfected cell lines, or genetically engineered tumors (e.g., such as by infection with a recombinant retroviral vector).

In one embodiment, the tissue microarray 13 comprises tissues from different recombinant inbred strains of individuals (e.g., mice). In a further embodiment, tissues from humans comprising a characterized haplotype are arrayed (e.g., a particular grouping of HLA alleles).

Embedding Tissues: Forming Donor Blocks

Although the device according to the invention is particularly suited for arraying frozen tissue, other types of embedded tissues may be arrayed using device (e.g., by setting the temperature of the cooling chamber 7 to room temperature, or alternatively removing the cooling chamber 7 from the platform 12 and seating the retaining chamber 6 on the platform 12).

In one embodiment of the invention, therefore, tissues are obtained and either paraffin-embedded, plastic-embedded, or frozen. When paraffin-embedded tissues are used, a variety of tissue fixation techniques can be used. Examples of fixatives, include, but are not limited to, aldehyde fixatives such as formaldehyde, formalin or formol, glyoxal, glutaraldehyde, hydroxyadipaldehyde, crotonaldehyde, methacrolein, acetaldehyde, pyruvic aldehyde, malonaldehyde, malialdehyde, and succinaldehyde; chloral hydrate; diethylpyrocarbonate; alcohols such as methanol and ethanol; acetone; lead fixatives such as basic lead acetates and lead citrate; mercuric salts such as mercuric chloride; formaldehyde; dichromate fluids; chromates; picric acid, and heat.

Tissues are fixed until they are sufficiently hard to embed. The type of fixative employed will be determined by the type of molecular procedure being used, e.g., where the molecular characteristic(s) being examined include the expression of nucleic acids, isopentane, or PVA, or another alcohol-based fixative is preferred, paraffin is preferred for performing immunohistochemistry, in situ hybridization, and in general, for tissues which are going to be stored for long periods of time. When cells are obtained from plasma, the cells may be snap frozen. OCT embedding is optimal for morphological evaluations.

Embedding media encompassed within the scope of the invention, includes, but is not limited to paraffin or other waxes, plastic, gelatin, agar, polyethylene glycols, polyvinyl alcohol, celloidin, nitrocelluloses, methyl and butyl methacrylate resins or epoxy resins. Water-insoluble embedding media such as paraffin and nitrocellulose require that specimens be dehydrated in several changes of solvent such as ethyl alcohol, acetone, xylene, toluene, benzene, petroleum, ether, chloroform, carbon tetrachloride, carbon bisulfide, and cedar oil, or isopropyl alcohol prior to immersion in a solvent in which the embedding medium is soluble. Water soluble embedding media such as polyvinyl alcohol, carbowax (polyethylene glycols), gelatin, and agar, can also be used.

In one embodiment, tissue specimens are freeze-dried by deep freezing in plastic tissue cassettes and storing them at −80–70° C., such as in liquid nitrogen. In one embodiment, the tissues are then covered with a cryogenic media, such as OCT®, and kept at −80–70° C., until sectioned. Examples of embedding media for frozen tissues include, but are not limited to, OCT, Histoprep®, TBS, CRYO-Gel®, and gelatin, to name a few. In another embodiment, a tissue freezing aerosol may be used to facilitate embedding of the donor frozen tissue block. An example of a freezing aerosol is tetrafluoroethane 2.2. Other methods known in the art may also be used to facilitate embedding of a tissue sample.

Forming the Recipient Block

While the order of the donor tissues in the recipient block is not critical, in some embodiments, donor tissue samples are spatially organized. For example, in one embodiment, donor tissues represent different stages of disease, such as cancer, and are ordered from least progressive to most progressive (e.g., associated with the lowest survival rates). In another embodiment, tissue samples within a microarray 13 will be ordered into groups which represent the patients from which the tissues are derived. For example, in one embodiment, the groupings are based on multiple patient parameters that can be reproducibly defined from the development of molecular disease profiles. In another embodiment, tissues are coded by genotype and/or phenotype. Tissue samples on the microarray 13 can additionally be arranged according to treatment approach, treatment outcome, or prognosis, or according to any other scheme that facilitates the subsequent analysis of the samples and the data associated with them.

The recipient block can be prepared while tissue samples are being obtained from the donor block. However, in one embodiment, the recipient block is prepared prior to obtaining samples from the donor block, for example, by placing a fast-freezing, cryo-embedding matrix in a container and freezing the matrix so as to create a solid, frozen block. The embedding matrix can be frozen using a tissue freezing aerosol such as tetrafluorethane 2.2 or by any other methods known in the art. The holes for holding tissue samples can be produced by punching holes of substantially the same dimensions into the recipient block as those of the donor frozen tissue samples and discarding the extra embedding matrix.

Information regarding the coordinates of the hole into which a tissue sample is placed and the identity of the tissue sample at that hole is recorded, effectively addressing each sublocation 13s on the microarray 13. In one embodiment of the invention, data relating to any, or all of, tissue type, stage of development or disease, individual of origin, patient history, family history, diagnosis, prognosis, medication, morphology, concurrent illnesses, expression of molecular characteristics (e.g., markers), and the like, is recorded and stored in a database, indexed according to the location of the tissue on the microarray 13. Data can be recorded at the same time that the microarray 13 is formed, or prior to, or after, formation of the microarray 13.

Customizing Tissue Microarrays

In one embodiment, information relating to desired coordinates identified by evaluating a representative section of a donor block is stored within the database of a tissue information system 98 (see FIG. 7). The tissue information system comprises both the database 102 and a tissue information management system 103 and at least one user device 100 connectable to the network 101 and to a server 104. The tissue information management system 103 comprises searching and relationship determining functions for accessing, organizing, and displaying tissue information to a user who has access to the system. The system 98 may additionally include output devices such as printers 105, to generate reports, and input devices 106, such as scanners.

In one embodiment, as shown in FIG. 8, the invention provides a system 16 for ordering customized microarrays 13 electronically using the tissue information system. In this embodiment, a first user is provided with access to an interface 17 which displays identifiers 18, each of which identifies a different tissue type (e.g., such as the tissue type of the tissues preserved in a plurality of donor blocks). The first user identifies tissue types of interest (e.g., by checking any of a plurality of circles 70 provided alongside an identifier 18 which identifies the tissue type), or obtains more information about the tissue types. In the latter embodiment, the tissue type identifier 18 is itself a link which, when selected, causes the system to display another interface (not shown) providing information about the tissue type/source, such as patient data, molecular profile data, and the like. In another embodiment of the invention, information relating to one or more coordinates identified from analysis of a representative section within a donor block is displayed, and the user is provided the option of selecting specific coordinates of interest in a donor block.

In a further embodiment, the interface 17 accessed by the first user provides field(s) 72 to enter query terms, and the system 16 displays tissue information relating to these query terms. For example, in one embodiment, the user enters keywords requesting information relating to lung cancer and exposure to asbestos, and the system displays identifiers 18 identifying tissues obtained from patients with lung cancer who have been exposed to asbestos. Selection of any of the identifiers 18 will communicate a request to the microarray generator 19 to provide these tissue(s) on the microarray 13. Microarray generators 19 encompassed within the scope of the invention include, but are not limited to a second user who operates a microarrayer device according to the invention, or the microarrayer device itself which is coupled to the system 16 by a processor which communicates with both the system 16 and the processor, directing movement of different elements of the microarrayer device in response to commands from the system 16.

In one embodiment, the microarrayer device is further coupled to a donor block storage container comprising a plurality of donor blocks, each block provided with an identifier (e.g., such as a microchip, scannable bar code, or radiofrequency transmitter). In this embodiment, when the first user identifies a donor block of interest using the system 16, a detector in communication with both the holder and the system 16 is used to identify the appropriate donor block (e.g., a block requested by a user of the system 16). The detector communicates that a block has been identified to the system 16 which in turn relays instructions to a robotic arm to select and grasp the appropriate donor block and place it within the retaining chamber 6 of the microarrayer device. In one embodiment, the detector for detecting the identifier on the block is part of the robotic arm itself.

Robotic arms and methods of using these to transfer identified substrates from one container to another are known in the art (see, e.g., U.S. Pat. Nos. 6,045,041; 6,035,245; 5,963,314; 5,920,477; 5,868,803; 5,836,735; 5,774,357; 5,740,270, the entireties of which are incorporated by reference herein). Methods for controlling the movement of various elements of workstations are also well known and described in, for example, U.S. Pat. Nos. 3,665,148; 4,484,293; 5,567,715; and 5,355,439, the entireties of which are incorporated by reference herein. Methods of programming robotic systems to perform designated tasks are also known in the art and are described, for example, in U.S. Pat. No. 4,835,730, the entirety of which is incorporated by reference herein.

In a further embodiment, the interface 17 of the system 16 further requests information from the first user such as billing information (credit card, account number, and the like), address, date required, and other shipping information. In additional embodiments, the user is also provided with the option to select nucleic acid arrays, peptide arrays, and/or other small biomolecule arrays, which may be arrayed on the same or different substrates as the tissue microarray 13.

Kits

The invention further provides kits. A kit according to the invention minimally contains a tissue microarray 13 and provides access to a tissue information system (e.g., as shown in FIG. 7) which provides a source of information about tissues on the microarray generated by the microarrayer device. In one embodiment, access is provided by providing a user of the microarray with a URL and an identifier which identifies the particular microarray being used, and/or a password to access the tissue information system. In one embodiment, the kit comprises instructions for accessing the database, or one or more molecular probes for obtaining molecular profiling data using the microarray 13, and/or other reagents necessary for performing molecular profiling (e.g., labels, suitable buffers, and the like). In one embodiment of the invention, the components of the kits are customized by a second user receiving information from a first user as described above.

Variations, modifications, and other implementations of what is described herein will occur to those of ordinary skill in the art without departing from the spirit and scope of the invention.

What is claimed is:

1. A method for forming a microarray block, comprising:
    (a) providing a donor block comprising a frozen tissue sample wherein said donor block is placed in a cooling chamber for receiving said frozen tissue sample and for maintaining said frozen tissue sample in a frozen condition;
    (b) obtaining a core of frozen tissue from said donor block;
    (c) providing a recipient block comprising a frozen embedding matrix;
    (d) generating a hole in said recipient block for receiving said core of frozen tissue; and
    (e) placing said core of tissue in said hole in said recipient block.

2. The method according to claim 1, comprising repeating steps (a) through (d) multiple times.

3. The method according to claim 1, further comprising the step of placing said donor and recipient blocks in said cooling chamber.

4. The method according to claim 1, wherein said step of obtaining said core of frozen tissue comprises coring said frozen tissue with a coring needle.

5. The method according to claim 1, further comprising:
    obtaining a section of tissue from said donor block and identifying coordinates of a tissue sample of interest in said section; and
    obtaining said core of frozen tissue from a portion of the donor block comprising identical coordinates.

6. The method according to claim 5, wherein said identifying is performed using a microscope.

7. The method according to claim 5, wherein said tissue sample of interest comprises abnormally proliferating cells.

8. The method according to claim 5, wherein said step of identifying comprises reacting said section with a molecular probe and identifying coordinates on said section where said tissue reacts with said molecular probe.

9. The method according to claim 5, wherein said step of identifying comprises reacting said section with a molecular probe and identifying coordinates on said section wherein said tissue does not react with said molecular probe.

10. The method according to claim 8 or 9, wherein said molecular probe is an antibody or a nucleic acid.

11. The method of claim 5, wherein said step of obtaining said core from said donor block and generating said hole in said recipient block are performed simultaneously.

12. The method of claim 5, wherein said step of obtaining said core from said donor block and creating said hole in said recipient block are performed sequentially.

13. A method for forming a microarray block comprising:
    (a) providing a donor block comprising a frozen tissue sample wherein said donor block is placed in a cooling chamber for receiving said frozen tissue sample and for maintaining said frozen tissue sample in a frozen condition;
    (b) providing a recipient block comprising a frozen embedding matrix comprising at least one hole for receiving a core of frozen tissue;
    (c) obtaining a core of frozen tissue from said donor block; and
    (d) placing said core of tissue in said hole in said recipient block.

14. A method for forming a microarray block comprising:
    a) providing a device comprising:
        a fixed horizontal surface;
        a cooling chamber for receiving at least one frozen material and for maintaining said frozen material in a frozen condition; said cooling chamber moveable in an x- and y-direction relative to said fixed horizontal surface;
        at least one coring needle, said coring needle comprising a cutting surface and a lumen for receiving a core of frozen material cut by said cutting surface; and
        at least one coring needle positioning element, for positioning said at least one coring needle over said frozen material for cutting said frozen material;
    b) placing a frozen tissue sample in said cooling chamber;
    c) positioning said at least one coring needle over said tissue sample;
    d) obtaining a core of tissue sample from said frozen tissue sample using said at least one coring needle;
    e) placing a block of frozen embedding medium in said cooling chamber;
    f) positioning said at least one coring needle over said block of frozen embedding medium;
    g) coring a hole in said block of frozen embedding medium; and
    h) placing said core of tissue sample in said hole.

15. The method according to claim 14, wherein said step of obtaining said core of tissue sample is performed using a first coring needle and said step of coring said hole in said block of frozen embedding medium is performed using a second coring needle.

16. The method according to claim 14 or 15, further comprising the step of pushing said core of tissue sample from said coring needle using a stylet, at least a portion of which slideably fits within said coring needle.

17. The method according to claim 16, wherein said stylet comprises a stylet needle comprising a pushing surface and which slideably fits within said coring needle and a resilient element, said resilient element for imparting linear force on a core of frozen material within said coring needle.

18. The method according to claim 15, further comprising the step of pushing a core of frozen embedding matrix cored by said second coring needle using a stylet, at least a portion of which slideably fits within said coring needle.

19. The method according to any of claims 5, 13, and 14, further comprising the step of sectioning said microarray block thereby obtaining a section comprising a plurality of sectioned tissue samples.

20. The method according to claim 19, further comprising the step of placing said section comprising said plurality of tissue samples on a substrate.

21. The method according to claim 20, wherein said substrate is a glass slide.

22. The method according to any of claims 5, 13, or 14, wherein information regarding the coordinates of a hole into which a tissue sample is placed and the identity of a tissue sample at that hole is recorded and stored in a database.

23. The method according to claim 22, wherein said database comprises patient information relating to the source of a tissue sample placed in said hole.

24. The method according to claim 23, wherein said information is one or more of:

data relating to tissue type, developmental stage, disease presence, disease progression, patient medical history, family medical history, and expression of one or more biomolecules in the tissue sample.

* * * * *